United States Patent
Terry, Jr.

(10) Patent No.: US 8,457,747 B2
(45) Date of Patent: Jun. 4, 2013

(54) NEUROSTIMULATION WITH SIGNAL DURATION DETERMINED BY A CARDIAC CYCLE

(75) Inventor: Reese S. Terry, Jr., Houston, TX (US)

(73) Assignee: Cyberonics, Inc., Houston, TX (US)

(*) Notice: Subject to any disclaimer, the term of this patent is extended or adjusted under 35 U.S.C. 154(b) by 337 days.

(21) Appl. No.: 12/254,595

(22) Filed: Oct. 20, 2008

(65) Prior Publication Data

US 2010/0100151 A1    Apr. 22, 2010

(51) Int. Cl.
*A61N 1/36* (2006.01)

(52) U.S. Cl.
USPC .......................................................... 607/45

(58) Field of Classification Search
None
See application file for complete search history.

(56) References Cited

U.S. PATENT DOCUMENTS

| | | | |
|---|---|---|---|
| 3,760,812 A | 9/1973 | Timm et al. | |
| 3,796,221 A | 3/1974 | Hagfors | |
| 4,107,469 A | 8/1978 | Jenkins | |
| 4,305,402 A | 12/1981 | Katims | |
| 4,338,945 A | 7/1982 | Kosugi et al. | |
| 4,424,812 A | 1/1984 | Lesnick | |
| 4,431,000 A | 2/1984 | Butler et al. | |
| 4,459,989 A | 7/1984 | Borkan | |
| 4,503,863 A | 3/1985 | Katims | |
| 4,541,432 A | 9/1985 | Molina-Negro et al. | |
| 4,573,481 A | 3/1986 | Bullara | |
| 4,577,316 A | 3/1986 | Schiff | |
| 4,590,946 A | 5/1986 | Loeb | |
| 4,592,339 A | 6/1986 | Kuzmak et al. | |
| 4,606,349 A | 8/1986 | Livingston et al. | |
| 4,608,985 A | 9/1986 | Crish et al. | |
| 4,612,934 A | 9/1986 | Borkan | |
| 4,625,308 A | 11/1986 | Kim et al. | |
| 4,628,942 A | 12/1986 | Sweeney et al. | |
| 4,649,936 A | 3/1987 | Ungar et al. | |
| 4,702,254 A | 10/1987 | Zabara | |
| 4,793,353 A | 12/1988 | Borkan | |
| 4,867,164 A | 9/1989 | Zabara ......................... 128/421 |

(Continued)

FOREIGN PATENT DOCUMENTS

| | | |
|---|---|---|
| CA | 2339971 | 6/2004 |
| EP | 0402683 A2 | 12/1990 |

(Continued)

OTHER PUBLICATIONS

Zhang et al., entitled; "Optimal ventricular rate slowing during atrial fibrillation by feedback AV nodal-selective vagal stimulation" which is an article incorporated by reference in the Gross disclosure (p. [0222]).*

(Continued)

*Primary Examiner* — Carl H Layno
*Assistant Examiner* — Paula J Stice
(74) *Attorney, Agent, or Firm* — Cyberonics, Inc.

(57) ABSTRACT

We disclose a method of providing an electrical signal to a cranial nerve of a patient for treating a medical condition, comprising providing an electrical signal generator, coupling at least a first electrode to a cranial nerve of the patient and to the electrical signal generator, generating an electrical signal with the electrical signal generator, and applying the electrical signal to the cranial nerve, using the at least a first electrode, for a duration less than a cardiac period of the patient and during the cardiac period of the patient. We also disclose an implantable medical device capable of implementing the method.

19 Claims, 6 Drawing Sheets

U.S. PATENT DOCUMENTS

| | | | |
|---|---|---|---|
| 4,920,979 A | 5/1990 | Bullara | |
| 4,949,721 A | 8/1990 | Toriu et al. | |
| 4,977,985 A | 12/1990 | Wells et al. | |
| 4,979,511 A | 12/1990 | Terry, Jr. | 128/642 |
| 5,025,807 A | 6/1991 | Zabara | |
| 5,081,987 A | 1/1992 | Nigam | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | 128/419 R |
| 5,205,285 A | 4/1993 | Baker, Jr. | |
| 5,215,086 A | 6/1993 | Terry, Jr. et al. | 128/421 |
| 5,222,494 A | 6/1993 | Baker, Jr. | |
| 5,231,988 A | 8/1993 | Wernicke et al. | 128/421 |
| 5,235,980 A | 8/1993 | Varrichio et al. | |
| 5,263,480 A | 11/1993 | Wernicke et al. | 607/118 |
| 5,269,303 A | 12/1993 | Wernicke et al. | 607/45 |
| 5,299,569 A | 4/1994 | Wernicke et al. | 607/45 |
| 5,304,206 A | 4/1994 | Baker, Jr. et al. | 607/2 |
| 5,330,507 A | 7/1994 | Schwartz | |
| 5,330,515 A | 7/1994 | Rutecki et al. | 607/46 |
| 5,334,221 A | 8/1994 | Bardy | |
| 5,335,657 A | 8/1994 | Terry, Jr. et al. | 607/45 |
| 5,354,320 A | 10/1994 | Schaldach et al. | |
| 5,411,531 A | 5/1995 | Hill et al. | |
| 5,411,540 A | 5/1995 | Edell et al. | |
| 5,423,872 A | 6/1995 | Cigaina | |
| 5,507,784 A | 4/1996 | Hill et al. | |
| 5,522,862 A | 6/1996 | Testerman et al. | |
| 5,522,865 A | 6/1996 | Schulman et al. | |
| 5,540,730 A | 7/1996 | Terry, Jr. et al. | |
| 5,540,734 A | 7/1996 | Zabara | |
| 5,571,150 A | 11/1996 | Wernicke et al. | 607/72 |
| 5,601,617 A | 2/1997 | Loeb et al. | |
| 5,611,350 A | 3/1997 | John | |
| 5,645,570 A | 7/1997 | Corbucci | |
| 5,651,378 A | 7/1997 | Matheny et al. | |
| 5,658,318 A | 8/1997 | Stroetmann et al. | |
| 5,690,681 A | 11/1997 | Geddes et al. | |
| 5,690,688 A | 11/1997 | Noren et al. | |
| 5,690,691 A | 11/1997 | Chen et al. | |
| 5,700,282 A | 12/1997 | Zabara | |
| 5,702,428 A | 12/1997 | Tippey et al. | |
| 5,702,429 A | 12/1997 | King | |
| 5,707,400 A | 1/1998 | Terry, Jr. et al. | 607/44 |
| 5,755,750 A | 5/1998 | Petruska et al. | |
| 5,792,212 A | 8/1998 | Weijand | |
| 5,800,474 A | 9/1998 | Benabid et al. | |
| 5,814,092 A | 9/1998 | King | |
| 5,836,994 A | 11/1998 | Bourgeois | |
| 5,861,014 A | 1/1999 | Familoni | |
| 5,913,882 A | 6/1999 | King | |
| 5,916,239 A | 6/1999 | Geddes et al. | 607/14 |
| 5,928,272 A | 7/1999 | Adkins et al. | 607/45 |
| 5,941,906 A | 8/1999 | Barreras, Sr. et al. | |
| 5,995,868 A | 11/1999 | Dorfmeister et al. | |
| 6,002,966 A | 12/1999 | Loeb et al. | |
| 6,016,449 A | 1/2000 | Fischell et al. | |
| 6,041,258 A | 3/2000 | Cigaina et al. | |
| 6,083,249 A | 7/2000 | Familoni | |
| 6,101,412 A | 8/2000 | Duhaylongsod | |
| 6,104,955 A | 8/2000 | Bourgeois | |
| 6,104,956 A | 8/2000 | Naritoku et al. | |
| 6,115,628 A | 9/2000 | Stadler et al. | |
| 6,132,361 A | 10/2000 | Epstein et al. | |
| 6,141,590 A | 10/2000 | Renirie et al. | |
| 6,161,044 A | 12/2000 | Silverstone | |
| 6,167,311 A | 12/2000 | Rezai | |
| 6,175,764 B1 | 1/2001 | Loeb et al. | |
| 6,188,929 B1 | 2/2001 | Giordano | |
| 6,219,580 B1 | 4/2001 | Faltys et al. | |
| 6,221,908 B1 | 4/2001 | Kilgard et al. | |
| 6,238,423 B1 | 5/2001 | Bardy | |
| 6,249,704 B1 | 6/2001 | Maltan et al. | |
| 6,253,109 B1 | 6/2001 | Gielen | |
| 6,266,564 B1 | 7/2001 | Hill et al. | |
| 6,269,270 B1 | 7/2001 | Boveja | |
| 6,295,472 B1 | 9/2001 | Rubinstein et al. | |
| 6,304,775 B1 | 10/2001 | Iasemidis et al. | |
| 6,308,102 B1 | 10/2001 | Sieracki et al. | |
| 6,324,421 B1 | 11/2001 | Stadler et al. | |
| 6,327,503 B1 | 12/2001 | Familoni | |
| 6,339,725 B1 | 1/2002 | Naritoku et al. | |
| 6,341,236 B1 | 1/2002 | Osorio et al. | |
| 6,353,762 B1 | 3/2002 | Baudino et al. | |
| 6,356,788 B2 | 3/2002 | Boveja | |
| 6,358,203 B2 | 3/2002 | Bardy | |
| 6,366,813 B1 | 4/2002 | DiLorenzo | |
| 6,366,814 B1 | 4/2002 | Boveja et al. | |
| 6,374,140 B1 | 4/2002 | Rise | |
| 6,381,493 B1 | 4/2002 | Stadler et al. | |
| 6,381,496 B1 | 4/2002 | Meadows et al. | |
| 6,381,499 B1 | 4/2002 | Taylor et al. | |
| 6,418,344 B1 | 7/2002 | Rezai et al. | |
| 6,425,852 B1 | 7/2002 | Epstein et al. | |
| 6,438,423 B1 | 8/2002 | Rezai et al. | |
| 6,449,512 B1 | 9/2002 | Boveja | |
| 6,453,199 B1 | 9/2002 | Kobozev | |
| 6,459,936 B2 | 10/2002 | Fischell et al. | |
| 6,463,328 B1 | 10/2002 | John | |
| 6,466,822 B1 | 10/2002 | Pless | |
| 6,473,639 B1 | 10/2002 | Fischell et al. | |
| 6,473,644 B1 | 10/2002 | Terry, Jr. et al. | |
| 6,477,417 B1 | 11/2002 | Levine | |
| 6,477,418 B2 | 11/2002 | Plicchi et al. | |
| 6,480,743 B1 | 11/2002 | Kirkpatrick et al. | |
| 6,484,132 B1 | 11/2002 | Hively et al. | |
| 6,487,446 B1 | 11/2002 | Hill et al. | |
| 6,505,074 B2 | 1/2003 | Boveja et al. | |
| 6,522,928 B2 | 2/2003 | Whitehurst et al. | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,565,503 B2 | 5/2003 | Leysieffer et al. | |
| 6,579,280 B1 | 6/2003 | Kovach et al. | |
| 6,587,719 B1 | 7/2003 | Barrett et al. | 607/2 |
| 6,587,724 B2 | 7/2003 | Mann | |
| 6,587,726 B2 | 7/2003 | Lurie et al. | |
| 6,587,727 B2 | 7/2003 | Osorio et al. | |
| 6,591,138 B1 | 7/2003 | Fischell et al. | |
| 6,594,524 B2 | 7/2003 | Esteller et al. | |
| 6,600,953 B2 | 7/2003 | Flesler et al. | |
| 6,609,025 B2 | 8/2003 | Barrett et al. | 607/2 |
| 6,609,030 B1 | 8/2003 | Rezai et al. | |
| 6,609,031 B1 | 8/2003 | Law et al. | |
| 6,610,713 B2 | 8/2003 | Tracey | |
| 6,611,715 B1 | 8/2003 | Boveja | |
| 6,612,983 B1 | 9/2003 | Marchal | |
| 6,615,081 B1 | 9/2003 | Boveja | |
| 6,615,084 B1 | 9/2003 | Cigaina | |
| 6,615,085 B1 | 9/2003 | Boveja | |
| 6,622,038 B2 | 9/2003 | Barrett et al. | |
| 6,622,041 B2 | 9/2003 | Terry, Jr. et al. | 607/9 |
| 6,622,047 B2 | 9/2003 | Barrett et al. | |
| 6,628,987 B1 | 9/2003 | Hill et al. | |
| 6,656,960 B2 | 12/2003 | Puskas | |
| 6,662,053 B2 | 12/2003 | Borkan | |
| 6,668,191 B1 | 12/2003 | Boveja | |
| 6,671,547 B2 | 12/2003 | Lyster et al. | |
| 6,671,555 B2 | 12/2003 | Gielen et al. | |
| 6,671,556 B2 | 12/2003 | Osorio et al. | |
| 6,684,104 B2 | 1/2004 | Gordon et al. | |
| 6,684,105 B2 | 1/2004 | Cohen et al. | |
| 6,690,973 B2 | 2/2004 | Hill et al. | |
| 6,690,974 B2 | 2/2004 | Archer et al. | |
| 6,708,064 B2 | 3/2004 | Rezai | |
| 6,721,603 B2 | 4/2004 | Zabara et al. | |
| 6,731,979 B2 | 5/2004 | MacDonald | |
| 6,731,986 B2 | 5/2004 | Mann | |
| 6,754,536 B2 | 6/2004 | Swoyer et al. | |
| 6,760,626 B1 | 7/2004 | Boveja | |
| 6,764,498 B2 | 7/2004 | Mische | |
| 6,768,969 B1 | 7/2004 | Nikitin et al. | |
| 6,775,573 B2 | 8/2004 | Schuler et al. | |
| 6,793,670 B2 | 9/2004 | Osorio et al. | |
| 6,819,956 B2 | 11/2004 | DiLorenzo | |

| | | | | | | |
|---|---|---|---|---|---|---|
| 6,826,428 B1 | 11/2004 | Chen et al. | | 2005/0021105 A1 | 1/2005 | Firlik et al. |
| 6,832,114 B1 | 12/2004 | Whitehurst et al. | | 2005/0021106 A1 | 1/2005 | Firlik et al. |
| 6,853,862 B1 | 2/2005 | Marchal et al. | | 2005/0021107 A1 | 1/2005 | Firlik et al. |
| 6,885,888 B2 | 4/2005 | Rezai | | 2005/0021118 A1 | 1/2005 | Genau et al. |
| 6,895,278 B1 | 5/2005 | Gordon | | 2005/0027284 A1 | 2/2005 | Lozano et al. |
| 6,904,390 B2 | 6/2005 | Nikitin et al. | | 2005/0028026 A1 | 2/2005 | Shirley et al. |
| 6,907,295 B2 | 6/2005 | Gross et al. | | 2005/0033378 A1 | 2/2005 | Sheffield et al. |
| 6,920,357 B2 | 7/2005 | Osorio et al. | | 2005/0033379 A1 | 2/2005 | Lozano et al. |
| 6,934,580 B1 | 8/2005 | Osorio et al. | | 2005/0038326 A1 | 2/2005 | Mathur |
| 6,944,501 B1 | 9/2005 | Pless | | 2005/0038484 A1 | 2/2005 | Knudson et al. |
| 6,961,618 B2 | 11/2005 | Osorio et al. | | 2005/0049515 A1 | 3/2005 | Misczynski et al. |
| 7,006,859 B1 | 2/2006 | Osorio et al. | | 2005/0049655 A1 | 3/2005 | Boveja et al. |
| 7,006,872 B2 | 2/2006 | Gielen et al. | | 2005/0060007 A1 | 3/2005 | Goetz |
| 7,050,856 B2 | 5/2006 | Stypulkowski | | 2005/0060008 A1 | 3/2005 | Goetz |
| 7,054,686 B2 | 5/2006 | MacDonald | | 2005/0060009 A1 | 3/2005 | Goetz |
| 7,146,217 B2 | 12/2006 | Firlik et al. | | 2005/0060010 A1 | 3/2005 | Goetz |
| 7,167,750 B2 | 1/2007 | Knudson et al. | | 2005/0065562 A1 | 3/2005 | Rezai |
| 7,177,678 B1 | 2/2007 | Osorio et al. | | 2005/0065573 A1 | 3/2005 | Rezai |
| 7,188,053 B2 | 3/2007 | Nikitin et al. | | 2005/0065574 A1 | 3/2005 | Rezai |
| 7,204,833 B1 | 4/2007 | Osorio et al. | | 2005/0065575 A1 | 3/2005 | Dobak |
| 7,209,787 B2 | 4/2007 | DiLorenzo | | 2005/0070971 A1 | 3/2005 | Fowler et al. |
| 7,231,254 B2 | 6/2007 | DiLorenzo | | 2005/0075679 A1 | 4/2005 | Gliner et al. |
| 7,236,830 B2 | 6/2007 | Gliner | | 2005/0075680 A1 | 4/2005 | Lowry et al. |
| 7,236,831 B2 | 6/2007 | Firlik et al. | | 2005/0075681 A1 | 4/2005 | Rezai et al. |
| 7,242,983 B2 | 7/2007 | Frei et al. | | 2005/0075691 A1 | 4/2005 | Phillips et al. |
| 7,242,984 B2 | 7/2007 | DiLorenzo | | 2005/0075701 A1 | 4/2005 | Shafer |
| 7,340,302 B1 | 3/2008 | Falkenberg et al. | | 2005/0075702 A1 | 4/2005 | Shafer |
| 2002/0072782 A1* | 6/2002 | Osorio et al. .................. 607/45 | | 2005/0088145 A1 | 4/2005 | Loch |
| 2003/0045909 A1 | 3/2003 | Gross et al. | | 2005/0101873 A1 | 5/2005 | Misczynski et al. |
| 2003/0181954 A1 | 9/2003 | Rezai | | 2005/0102002 A1 | 5/2005 | Salo et al. |
| 2003/0181958 A1 | 9/2003 | Dobak, III | | 2005/0107753 A1 | 5/2005 | Rezai et al. |
| 2003/0181959 A1 | 9/2003 | Dobak, III | | 2005/0107842 A1 | 5/2005 | Rezai |
| 2003/0208212 A1 | 11/2003 | Cigaina | | 2005/0107858 A1 | 5/2005 | Bluger |
| 2003/0210147 A1 | 11/2003 | Humbard | | 2005/0113705 A1 | 5/2005 | Fischell et al. |
| 2003/0212440 A1 | 11/2003 | Boveja | | 2005/0113744 A1 | 5/2005 | Donoghue et al. |
| 2003/0236558 A1 | 12/2003 | Whitehurst et al. | | 2005/0119703 A1 | 6/2005 | DiLorenzo |
| 2004/0006278 A1 | 1/2004 | Webb et al. | | 2005/0124901 A1 | 6/2005 | Misczynski et al. |
| 2004/0015205 A1 | 1/2004 | Whitehurst et al. | | 2005/0131467 A1 | 6/2005 | Boveja |
| 2004/0036377 A1 | 2/2004 | Mezinis | | 2005/0131485 A1 | 6/2005 | Knudson et al. |
| 2004/0039424 A1 | 2/2004 | Merritt et al. | | 2005/0131486 A1 | 6/2005 | Boveja et al. |
| 2004/0088024 A1 | 5/2004 | Firlik et al. | | 2005/0131493 A1 | 6/2005 | Boveja et al. |
| 2004/0111139 A1 | 6/2004 | McCreery | | 2005/0131506 A1 | 6/2005 | Rezai et al. |
| 2004/0112894 A1 | 6/2004 | Varma | | 2005/0137480 A1 | 6/2005 | Alt et al. |
| 2004/0122484 A1 | 6/2004 | Hatlestad et al. | | 2005/0143779 A1 | 6/2005 | Libbus |
| 2004/0122485 A1 | 6/2004 | Stahmann et al. | | 2005/0143781 A1 | 6/2005 | Carbunaru et al. |
| 2004/0122489 A1 | 6/2004 | Mazar et al. | | 2005/0143786 A1 | 6/2005 | Boveja |
| 2004/0133119 A1 | 7/2004 | Osorio et al. | | 2005/0148893 A1 | 7/2005 | Misczynski et al. |
| 2004/0138516 A1 | 7/2004 | Osorio et al. | | 2005/0148894 A1 | 7/2005 | Misczynski et al. |
| 2004/0138517 A1 | 7/2004 | Osorio et al. | | 2005/0148895 A1 | 7/2005 | Misczynski et al. |
| 2004/0138518 A1 | 7/2004 | Rise et al. | | 2005/0153885 A1 | 7/2005 | Yun et al. |
| 2004/0138647 A1 | 7/2004 | Osorio et al. | | 2005/0154425 A1 | 7/2005 | Boveja et al. |
| 2004/0138711 A1 | 7/2004 | Osorio et al. | | 2005/0154435 A1 | 7/2005 | Stern et al. |
| 2004/0147969 A1 | 7/2004 | Mann et al. | | 2005/0159789 A1 | 7/2005 | Brockway et al. |
| 2004/0147992 A1 | 7/2004 | Bluger et al. | | 2005/0161052 A1 | 7/2005 | Rezai et al. |
| 2004/0153129 A1 | 8/2004 | Pless et al. | | 2005/0165458 A1 | 7/2005 | Boveja et al. |
| 2004/0158119 A1 | 8/2004 | Osorio et al. | | 2005/0177192 A1 | 8/2005 | Rezai et al. |
| 2004/0158165 A1 | 8/2004 | Yonce et al. | | 2005/0177200 A1 | 8/2005 | George et al. |
| 2004/0167583 A1 | 8/2004 | Knudson et al. | | 2005/0177206 A1 | 8/2005 | North et al. |
| 2004/0167587 A1 | 8/2004 | Thompson | | 2005/0182389 A1 | 8/2005 | LaPorte et al. |
| 2004/0172085 A1 | 9/2004 | Knudson et al. | | 2005/0187590 A1 | 8/2005 | Boveja et al. |
| 2004/0172088 A1 | 9/2004 | Knudson et al. | | 2005/0187593 A1 | 8/2005 | Housworth et al. |
| 2004/0172089 A1 | 9/2004 | Whitehurst et al. | | 2005/0187796 A1 | 8/2005 | Rosenfeld et al. |
| 2004/0172091 A1 | 9/2004 | Rezai | | 2005/0192644 A1 | 9/2005 | Boveja et al. |
| 2004/0172094 A1 | 9/2004 | Cohen et al. | | 2005/0197590 A1 | 9/2005 | Osorio et al. |
| 2004/0176812 A1 | 9/2004 | Knudson et al. | | 2005/0222631 A1 | 10/2005 | Dalal et al. |
| 2004/0176831 A1 | 9/2004 | Gliner et al. | | 2005/0228693 A1 | 10/2005 | Webb et al. |
| 2004/0193231 A1 | 9/2004 | David et al. | | 2005/0240246 A1 | 10/2005 | Lee et al. |
| 2004/0199146 A1 | 10/2004 | Rogers et al. | | 2005/0245944 A1 | 11/2005 | Rezai |
| 2004/0199187 A1 | 10/2004 | Loughran | | 2005/0245971 A1 | 11/2005 | Brockway et al. |
| 2004/0199212 A1 | 10/2004 | Fischell et al. | | 2005/0245990 A1 | 11/2005 | Roberson |
| 2004/0210270 A1 | 10/2004 | Erickson | | 2005/0261542 A1 | 11/2005 | Riehl |
| 2004/0210274 A1 | 10/2004 | Bauhahn et al. | | 2005/0267542 A1 | 12/2005 | David et al. |
| 2004/0249302 A1 | 12/2004 | Donoghue et al. | | 2005/0267550 A1 | 12/2005 | Hess et al. |
| 2004/0249416 A1 | 12/2004 | Yun et al. | | 2005/0272280 A1 | 12/2005 | Osypka |
| 2004/0260346 A1 | 12/2004 | Overall et al. | | 2005/0277872 A1 | 12/2005 | Colby, Jr. et al. |
| 2004/0263172 A1 | 12/2004 | Gray et al. | | 2005/0277998 A1 | 12/2005 | Tracey et al. |
| 2005/0004615 A1 | 1/2005 | Sanders | | 2005/0283200 A1 | 12/2005 | Rezai et al. |
| 2005/0004621 A1 | 1/2005 | Boveja et al. | | 2005/0283201 A1 | 12/2005 | Machado et al. |
| 2005/0010262 A1 | 1/2005 | Rezai et al. | | 2005/0283208 A1 | 12/2005 | Von Arx et al. |

| | | | | | | |
|---|---|---|---|---|---|---|
| 2005/0288600 A1 | 12/2005 | Zhang et al. | | 2007/0142873 A1 | 6/2007 | Esteller et al. |
| 2005/0288736 A1 | 12/2005 | Persen et al. | | 2007/0149952 A1 | 6/2007 | Bland et al. |
| 2005/0288760 A1 | 12/2005 | Machado et al. | | 2007/0150011 A1 | 6/2007 | Meyer et al. |
| 2006/0009815 A1 | 1/2006 | Boveja et al. | | 2007/0150014 A1 | 6/2007 | Kramer et al. |
| 2006/0020292 A1 | 1/2006 | Goetz et al. | | 2007/0150024 A1 | 6/2007 | Leyde et al. |
| 2006/0020491 A1 | 1/2006 | Mongeon et al. | | 2007/0150025 A1 | 6/2007 | Dilorenzo et al. |
| 2006/0041222 A1 | 2/2006 | Dewing et al. | | 2007/0156179 A1 | 7/2007 | S.E. |
| 2006/0041223 A1 | 2/2006 | Dewing et al. | | 2007/0156450 A1 | 7/2007 | Roehm et al. |
| 2006/0041287 A1 | 2/2006 | Dewing et al. | | 2007/0156626 A1 | 7/2007 | Roehm et al. |
| 2006/0047205 A1 | 3/2006 | Ludomirsky et al. | | 2007/0161919 A1 | 7/2007 | DiLorenzo |
| 2006/0052843 A1 | 3/2006 | Elsner et al. | | 2007/0162086 A1 | 7/2007 | DiLorenzo |
| 2006/0058597 A1 | 3/2006 | Machado et al. | | 2007/0167991 A1 | 7/2007 | DiLorenzo |
| 2006/0064133 A1 | 3/2006 | Von Arx et al. | | 2007/0173901 A1 | 7/2007 | Reeve |
| 2006/0064134 A1 | 3/2006 | Mazar et al. | | 2007/0179534 A1 | 8/2007 | Firlik et al. |
| 2006/0064143 A1 | 3/2006 | Von Arx et al. | | 2007/0179584 A1 | 8/2007 | Gliner |
| 2006/0069322 A1 | 3/2006 | Zhang et al. | | 2007/0203548 A1 | 8/2007 | Pawelzik et al. |
| 2006/0074450 A1 | 4/2006 | Boveja et al. | | 2007/0208212 A1 | 9/2007 | DiLorenzo |
| 2006/0079936 A1 | 4/2006 | Boveja et al. | | 2007/0208390 A1 | 9/2007 | Von Arx et al. |
| 2006/0079942 A1 | 4/2006 | Deno et al. | | 2007/0213785 A1 | 9/2007 | Osorio et al. |
| 2006/0079945 A1 | 4/2006 | Libbus | | 2007/0233192 A1 | 10/2007 | Craig |
| 2006/0085046 A1 | 4/2006 | Rezai et al. | | 2007/0233194 A1* | 10/2007 | Craig ................................ 607/2 |
| 2006/0094971 A1 | 5/2006 | Drew | | 2007/0238939 A1 | 10/2007 | Giftakis et al. |
| 2006/0095081 A1 | 5/2006 | Zhou et al. | | 2007/0239210 A1 | 10/2007 | Libbus et al. |
| 2006/0100667 A1* | 5/2006 | Machado et al. | | 2007/0239211 A1 | 10/2007 | Lorincz et al. |
| 2006/0100668 A1* | 5/2006 | Ben-David et al. ................ 607/2 | | 2007/0239220 A1 | 10/2007 | Greenhut et al. |
| 2006/0106430 A1 | 5/2006 | Fowler et al. | | 2007/0244407 A1 | 10/2007 | Osorio |
| 2006/0106431 A1 | 5/2006 | Wyler et al. | | 2007/0249953 A1 | 10/2007 | Frei et al. |
| 2006/0111644 A1 | 5/2006 | Guttag et al. | | 2007/0249954 A1 | 10/2007 | Virag et al. |
| 2006/0122525 A1 | 6/2006 | Shusterman | | 2007/0250130 A1 | 10/2007 | Ball et al. |
| 2006/0122667 A1 | 6/2006 | Chavan et al. | | 2007/0250145 A1 | 10/2007 | Kraus et al. |
| 2006/0122864 A1 | 6/2006 | Gottesman et al. | | 2007/0255147 A1 | 11/2007 | Drew et al. |
| 2006/0135877 A1 | 6/2006 | Giftakis et al. | | 2007/0255155 A1 | 11/2007 | Drew et al. |
| 2006/0135881 A1 | 6/2006 | Giftakis et al. | | 2007/0255330 A1 | 11/2007 | Lee et al. |
| 2006/0155495 A1 | 7/2006 | Osorio et al. | | 2007/0255337 A1 | 11/2007 | Lu |
| 2006/0161459 A9 | 7/2006 | Rosenfeld et al. | | 2007/0260147 A1 | 11/2007 | Giftakis et al. |
| 2006/0167497 A1 | 7/2006 | Armstrong et al. | | 2007/0260289 A1 | 11/2007 | Giftakis et al. |
| 2006/0173493 A1 | 8/2006 | Armstrong et al. | | 2007/0265489 A1 | 11/2007 | Fowler et al. |
| 2006/0173522 A1 | 8/2006 | Osorio | | 2007/0265508 A1 | 11/2007 | Sheikhzadeh-Nadjar et al. |
| 2006/0190056 A1 | 8/2006 | Fowler et al. | | 2007/0265536 A1 | 11/2007 | Giftakis et al. |
| 2006/0195155 A1 | 8/2006 | Firlik et al. | | 2007/0272260 A1 | 11/2007 | Nikitin et al. |
| 2006/0195163 A1 | 8/2006 | KenKnight et al. | | 2007/0282177 A1 | 12/2007 | Pilz |
| 2006/0200206 A1 | 9/2006 | Firlik et al. | | 2007/0287931 A1 | 12/2007 | Dilorenzo |
| 2006/0212091 A1 | 9/2006 | Lozano et al. | | 2007/0288072 A1 | 12/2007 | Pascual-Leone et al. |
| 2006/0217780 A1 | 9/2006 | Gliner et al. | | 2007/0299349 A1 | 12/2007 | Alt et al. |
| 2006/0220839 A1 | 10/2006 | Fifolt et al. | | 2007/0299473 A1 | 12/2007 | Matos |
| 2006/0224067 A1 | 10/2006 | Giftakis et al. | | 2007/0299480 A1 | 12/2007 | Hill |
| 2006/0224191 A1 | 10/2006 | Dilorenzo | | 2008/0015651 A1 | 1/2008 | Ettori et al. |
| 2006/0241697 A1 | 10/2006 | Libbus et al. | | 2008/0015652 A1 | 1/2008 | Maile et al. |
| 2006/0241725 A1 | 10/2006 | Libbus et al. | | 2008/0021332 A1 | 1/2008 | Brainard, III |
| 2006/0253164 A1 | 11/2006 | Zhang et al. | | 2008/0021341 A1 | 1/2008 | Harris et al. |
| 2006/0253168 A1 | 11/2006 | Wyler et al. | | 2008/0021504 A1 | 1/2008 | McCabe et al. |
| 2006/0253169 A1 | 11/2006 | Wyler et al. | | 2008/0021517 A1 | 1/2008 | Dietrich |
| 2006/0253170 A1 | 11/2006 | Wyler et al. | | 2008/0021520 A1 | 1/2008 | Dietrich |
| 2006/0253171 A1 | 11/2006 | Wyler et al. | | 2008/0027347 A1 | 1/2008 | Harris et al. |
| 2006/0259095 A1 | 11/2006 | Wyler et al. | | 2008/0027348 A1 | 1/2008 | Harris et al. |
| 2006/0264730 A1 | 11/2006 | Stivoric et al. | | 2008/0027515 A1 | 1/2008 | Harris et al. |
| 2006/0265018 A1 | 11/2006 | Smith et al. | | 2008/0033502 A1 | 2/2008 | Harris et al. |
| 2006/0271409 A1 | 11/2006 | Rosenfeld et al. | | 2008/0033503 A1 | 2/2008 | Fowler et al. |
| 2006/0293720 A1 | 12/2006 | DiLorenzo | | 2008/0033508 A1 | 2/2008 | Frei et al. |
| 2007/0027486 A1 | 2/2007 | Armstrong | | 2008/0039895 A1 | 2/2008 | Fowler et al. |
| 2007/0032734 A1 | 2/2007 | Najafi et al. | | 2008/0046035 A1 | 2/2008 | Fowler et al. |
| 2007/0032834 A1 | 2/2007 | Gliner et al. | | 2008/0046037 A1 | 2/2008 | Haubrich et al. |
| 2007/0038262 A1 | 2/2007 | Kieval et al. | | 2008/0046038 A1 | 2/2008 | Hill et al. |
| 2007/0043392 A1 | 2/2007 | Gliner et al. | | 2008/0051852 A1 | 2/2008 | Dietrich et al. |
| 2007/0055320 A1 | 3/2007 | Weinand | | 2008/0058884 A1 | 3/2008 | Matos |
| 2007/0073150 A1 | 3/2007 | Gopalsami et al. | | 2008/0064934 A1 | 3/2008 | Frei et al. |
| 2007/0073346 A1 | 3/2007 | Corbucci | | 2008/0071323 A1 | 3/2008 | Lowry et al. |
| 2007/0073355 A1 | 3/2007 | Dilorenzo | | 2008/0077028 A1 | 3/2008 | Schaldach et al. |
| 2007/0078491 A1 | 4/2007 | Siejko et al. | | 2008/0081962 A1 | 4/2008 | Miller et al. |
| 2007/0088403 A1 | 4/2007 | Wyler et al. | | 2008/0082132 A1 | 4/2008 | Annest et al. |
| 2007/0088404 A1 | 4/2007 | Wyler et al. | | 2008/0103548 A1 | 5/2008 | Fowler et al. |
| 2007/0088405 A1 | 4/2007 | Jacobson | | 2008/0114417 A1 | 5/2008 | Leyde |
| 2007/0100278 A1 | 5/2007 | Frei et al. | | 2008/0119900 A1 | 5/2008 | DiLorenzo |
| 2007/0100397 A1 | 5/2007 | Seeberger et al. | | 2008/0125820 A1 | 5/2008 | Stahmann et al. |
| 2007/0100398 A1 | 5/2007 | Sloan | | 2008/0139870 A1 | 6/2008 | Gliner et al. |
| 2007/0112393 A1 | 5/2007 | Gliner | | 2008/0146890 A1 | 6/2008 | LeBoeuf et al. |
| 2007/0123946 A1 | 5/2007 | Masoud | | 2008/0146959 A1 | 6/2008 | Sheffield et al. |
| 2007/0135855 A1 | 6/2007 | Foshee et al. | | 2008/0161712 A1 | 7/2008 | Leyde |
| 2007/0142862 A1 | 6/2007 | Dilorenzo | | 2008/0161713 A1 | 7/2008 | Leyde et al. |

| | | | |
|---|---|---|---|
| 2008/0161879 | A1 | 7/2008 | Firlik et al. |
| 2008/0161880 | A1 | 7/2008 | Firlik et al. |
| 2008/0161881 | A1 | 7/2008 | Firlik et al. |
| 2008/0161882 | A1 | 7/2008 | Firlik et al. |
| 2008/0183096 | A1 | 7/2008 | Snyder et al. |
| 2008/0183097 | A1 | 7/2008 | Leyde et al. |
| 2008/0183245 | A1 | 7/2008 | Van Oort et al. |
| 2008/0195175 | A1 | 8/2008 | Balzer et al. |
| 2008/0200925 | A1 | 8/2008 | Johnson et al. |
| 2008/0208013 | A1 | 8/2008 | Zhang et al. |
| 2008/0208074 | A1 | 8/2008 | Snyder et al. |
| 2008/0208285 | A1 | 8/2008 | Fowler et al. |
| 2008/0208291 | A1 | 8/2008 | Leyde et al. |
| 2008/0208781 | A1 | 8/2008 | Snyder |
| 2008/0215112 | A1 | 9/2008 | Firlik et al. |
| 2008/0215114 | A1 | 9/2008 | Stuerzinger et al. |
| 2008/0221644 | A1 | 9/2008 | Vallapureddy et al. |
| 2008/0234598 | A1 | 9/2008 | Snyder et al. |
| 2008/0249591 | A1 | 10/2008 | Gaw et al. |
| 2008/0255582 | A1 | 10/2008 | Harris |
| 2009/0054795 | A1 | 2/2009 | Misczynski et al. |
| 2009/0076567 | A1 | 3/2009 | Fowler et al. |

FOREIGN PATENT DOCUMENTS

| | | |
|---|---|---|
| EP | 0713714 A2 | 5/1996 |
| EP | 1647300 A2 | 2/1998 |
| EP | 1070518 A2 | 1/2001 |
| EP | 1120130 A2 | 1/2001 |
| EP | 1145736 A2 | 10/2001 |
| EP | 1304135 A | 4/2003 |
| EP | 1595497 A1 | 5/2004 |
| EP | 1486232 A2 | 12/2004 |
| GB | 2026870 A | 2/1980 |
| GB | 2079610 A | 1/1982 |
| WO | 9302744 A1 | 2/1993 |
| WO | 9417771 A2 | 8/1994 |
| WO | 98/19739 A | 5/1998 |
| WO | 9825688 A1 | 6/1998 |
| WO | 0040143 A1 | 7/2000 |
| WO | 0064336 A1 | 11/2000 |
| WO | 0064336 C2 | 11/2000 |
| WO | 0105467 A1 | 1/2001 |
| WO | 0108749 A1 | 2/2001 |
| WO | 03076010 A1 | 9/2003 |
| WO | 03085546 A1 | 10/2003 |
| WO | 2004036377 A2 | 4/2004 |
| WO | 2004064918 A1 | 8/2004 |
| WO | 2004071575 A1 | 8/2004 |
| WO | 2004075982 A1 | 9/2004 |
| WO | 2004112894 A1 | 12/2004 |
| WO | 2005007120 A2 | 1/2005 |
| WO | 2005007232 A2 | 1/2005 |
| WO | 2005028026 A1 | 3/2005 |
| WO | 2005053788 A1 | 6/2005 |
| WO | 2005067599 A2 | 7/2005 |
| WO | 2004069330 A1 | 8/2005 |
| WO | 2005101282 A2 | 10/2005 |
| WO | 2006014760 A1 | 2/2006 |
| WO | 2006019822 A2 | 2/2006 |
| WO | 2006050144 A1 | 5/2006 |
| WO | 2006122148 A2 | 11/2006 |
| WO | 2007066343 A2 | 6/2007 |
| WO | 2007072425 A2 | 6/2007 |
| WO | 2007115118 A | 10/2007 |
| WO | 2007124126 A2 | 11/2007 |
| WO | 2007124190 A2 | 11/2007 |
| WO | 2007124192 A1 | 11/2007 |
| WO | 2007142523 A1 | 12/2007 |

OTHER PUBLICATIONS

PCT Search Report for International Application No. PCT/US2009/005680 dated Apr. 2, 2010.
Lockard et al., "Feasibility and Safety of Vagal Stimulation in Monkey Model;" Epilepsia, vol. 31 (Supp. 2) (1990), pp. S20-S26.
Bachman, D.,S. et al.; "Effects of Vagal Volleys and Serotonin on Units of Cingulate Cortex in Monkeys;" Brain Research , vol. 130 (1977). pp. 253-269.
Terry et al.; "The Implantable Neurocybernetic Prosthesis System", Pacing and Clinical Electrophysiology, vol. 14, No. 1 (Jan. 1991), pp. 86-93.
Bohning, D.E., et al.; "Feasibility of Vagus Nerve Stimulation—Synchronized Blood Oxygenation Level-Dependent Functional MRI;" A Journal of Clinical and Laboratory Research: Investigative Radiology; vol. 36, No. 8 (Aug. 2001); pp. 470-479.
Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.
Clark, K.B., et al.; "Posttraining Electrical Stimulation of Vagal Afferents with Concomitant Vagal Efferent Inactivation Enhances Memory Storage Processes in the Rat;" Neurobiology of Learning and Memory, vol. 70, 364-373 (1998).
Clark, K.B., et al.; "Enhanced Recognition Memory Following Vagus Nerve Stimulation in Human Subjects;" Nature Neuroscience, vol. 2, No. 1, (Jan. 1999) pp. 93-98.
DeGiorgo, Christopher M., et al.; "Vagus Nerve Stimulation: Analysis of Device Parameters in 154 Patients During the Long-Term XE5 Study;" Epilepsia, vol. 42, No. 8; pp. 1017-1020 (2001).
Devous, Michael D., et al.; "Effects of Vagus Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.
Dodrill, Ph.D., et al.; "Effects of Vagal Nerve Stimulation on Cognition and Quality of Life in Epilepsy;" Epilepsy and Behavior, vol. 2 (2001); pp. 46-53.
Fanselow, E. E., et al.; "Reduction of Pentylenetetrazole-Induced Seizure Activity in Awake Rats by Seizure-Triggered Trigeminal Nerve Stimulation;" The Journal of Neuroscience, vol. 20, No. 21; (Nov. 2000); pp. 8160-8168.
George, M.S., et al.; "Open Trial of VNS Therapy in Severe Anxiety Disorders;" 156th American Psychiatric Association Annual Meeting; May 17-22, 2003.
George, M.S., et al.; "Vagus Nerve Stimulation: A New Tool for Brain Research and Therapy;" Society of Biological Psychiatry vol. 47 (2000) pp. 287-295.
Hallowitz, R.A., et al.; "Effects of Vagal Volleys on Units of Intralaminar and Juxtalaminar Thalamic Nuclei in Monkeys;" Brain Research, vol. 130 (1977), pp. 271-286.
Henry, MD, T.R.; "Therapeutic Mechanisms of Vagus Nerve Stimulation" Neurology, vol. 59 Suppl. 4 (Sep. 2002); pp. S3-S14.
King, M.D., "Effects of Short-Term Vagus Nerve Stimulation (VNS) on FOS Expression in Rat Brain Nuclei" 58th Annual Scientific Convention of the Society of Biological Psychiatry, (May 2003).
Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).
Koo, B., "EEG Changes With Vagus Nerve Stimulation" Journal of Clinical Neurophysiology, vol. 18 No. 5 (Sep. 2001); pp. 434-441.
Labar, D., "Vagus Nerve Stimulation for 1 Year in 269 patients on Unchanged Antiepilectic Drugs" Seizure vol. 13, (2004) pp. 392-398.
Liebman, K.M. et al.; "Improvement in Cognitive Function After Vagal Nerve Stimulator Implantation;" Epilepsia, vol. 39, Suppl. 6 (1998) 1 page.
Malow, B.A., et al.; "Vagus Nerve Stimulation Reduces Daytime Sleepiness in Epilepsy Patients" Neurology 57 (2001) pp. 879-884.
McClintock, P., "Can Noise Actually Boost Brain Power" Physics World Jul. 2002; pp. 20-21.
Mori, T., et al.; "Noise-Induced Entrainment and Stochastic Resonance in Human Brain Waves" Physical Review Letters vol. 88, No. 21 (May 2002); pp. 218101-1-218101-4.
Rugg-Gunn, F.J., et al.; "Cardiac Arrhythmias in Focal Epilepsy: a Prospective Long-Term Study" www.thelancet.com vol. 364 (2004) pp. 2212-2219.
Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents;" IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation;" Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdes-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck et al. "The Mechanism of Action of Vagus Nerve Stimulation for Refractory Epilepsy", Journal of Clinical Neurophysiology, vol. 18(5) (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Zabara, J. "Inhibition of Experimental Seizures in Canines by Repetivie Vagal Stimulation" Epilepsia vol. 33, No. 6 (1992); pp. 1005-1012.

Fromes, G., et al.; "Clinical Utility of On-Demand Magnet Use with Vagus Nerve Stimulation;" AES Proceedings.

Craig, A.D. (Bud); "Distribution of Trigeminothalamic and Spinothalamic Lamina I Terminations in the Macaque Monkey;" The Journal of Comparative Neurology, vol. 477, pp. 119-148 (2004).

Harry, J.D., et al.; "Balancing Act: Noise is the Key to Restoring the Body's Sense of Equilibrium;" IEEE Spectrum (Apr. 2005) pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

* cited by examiner

NEUROSTIMULATION WITH SIGNAL DURATION DETERMINED BY A CARDIAC CYCLE

BACKGROUND OF THE INVENTION

This invention relates generally to medical device systems and, more particularly, to medical device systems for applying electrical signals to a cranial nerve for the treatment of various medical conditions at particular times and for particular durations determined by a patient's cardiac cycle.

Many advancements have been made in treating diseases such as depression and epilepsy. Therapies using electrical signals for treating these diseases have been found to effective. Implantable medical devices (IMDs) have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electromagnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electromagnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

In some embodiments, electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. In yet another type of stimulation, both passive stimulation and feedback stimulation be combined, in which electrical signals are delivered passively according to a predetermined duty cycle, and also in response to a sensed body parameter. The electrical signal may be applied by a pulse generator that is implanted within the patient's body. In another alternative embodiment, the signal may be generated by an external pulse generator outside the patient's body, coupled by an RF or wireless link to an implanted electrode or an external transcutaneous neurostimulator (TNS).

Generally, neurostimulation signals that perform neuromodulation are delivered by the IMD via one (i.e., unipolar) or more (i.e., bipolar) leads. The leads generally terminate at their distal ends in one or more electrodes, and the electrodes, in turn, are electrically coupled to tissue in the patient's body. For example, a number of electrodes may be attached to various points of a nerve or other tissue inside or outside a human body for delivery of a neurostimulation signal.

Conventional vagus nerve stimulation (VNS) usually involves non-feedback stimulation characterized by a number of parameters. Specifically, conventional vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 7-60 seconds. The pulse bursts are separated from one another by the off-time, (e.g., 14 seconds-5 minutes) in which no electrical signal is applied to the nerve. The on-time and off-time parameters together define a duty cycle, which is the ratio of the on-time to the sum of the on-time and off-time, and which describes the percentage of time that the electrical signal is applied to the nerve. It will be appreciated that calculation of duty cycle should also include any ramp-up and/or ramp-down time.

In conventional VNS, the on-time and off-time may be programmed to define an intermittent pattern in which a repeating series of electrical pulse bursts are generated and applied to the vagus nerve 127. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

Although neurostimulation has proven effective in the treatment of a number of medical conditions, including epilepsy, it would be desirable to further enhance and optimize a therapeutic regimen comprising neurostimulation for this purpose. For example, it may be desirable to collect other data, either directly or indirectly associated with an acute incident of the medical condition, in order to inform the patient and/or his physician about the severity, progression, or remission of the medical condition. To do so, it may be desirable to provide a neurostimulation off-time during which the other data may be collected.

SUMMARY OF THE INVENTION

In one embodiment, the present invention relates to a method of providing an electrical signal to a cranial nerve of a patient for treating a medical condition, comprising providing an electrical signal generator, coupling at least a first electrode to a cranial nerve of the patient and to the electrical signal generator, generating an electrical signal with the electrical signal generator, and applying the electrical signal to the cranial nerve using the at least first electrode, wherein said electrical signal is applied to the cranial nerve for a duration determined by a cardiac cycle parameter of the patient. In one embodiment, the cardiac cycle parameter of the patient may comprise an R-R interval, another interbeat interval of the patient's cardiac cycle, or cardiac cycle components such as a P wave interval, a PR segment interval, a PQ segment interval, a QRS interval, or an ST segment interval. In another embodiment, applying the electrical signal to the cranial nerve is initiated at a time determined by a cardiac cycle parameter of the patient.

In another embodiment, in a method of providing an electrical signal to a cranial nerve of a patient for treating a medical condition, the present invention relates to the improvement comprising providing the electrical signal to the cranial nerve, wherein said electrical signal is applied to the cranial nerve for a duration determined by a cardiac cycle parameter of the patient.

In an additional embodiment, the present invention relates to an implantable medical device (IMD) comprising an electrical signal generator; a first electrode and a second electrode operatively coupled to the electrical signal generator; and a cardiac cycle determination module capable of determining a cardiac cycle of a patient; wherein: the electrical signal generator is capable of generating and delivering at least one electrical signal through at least one of the first electrode and the second electrode, wherein applying said electrical signal is applied to the cranial nerve for a duration determined by a cardiac cycle parameter of the patient.

In one embodiment, the present invention relates to a method of providing an electrical signal to a cranial nerve of a patient for treating a medical condition, comprising providing an electrical signal generator, coupling at least a first electrode to a cranial nerve of the patient and to the electrical signal generator, generating an electrical signal with the electrical signal generator, and applying the electrical signal to the cranial nerve, using the at least a first electrode, for a duration determined by a cardiac cycle of the patient. In a further embodiment, the method further comprises beginning to apply said electrical signal at a predetermined time in the cardiac cycle of the patient. The predetermined time may follow a delay period following detection of an R-wave in the cardiac cycle of the patient, or may comprise a predetermined multiple of an interbeat interval in the cardiac cycle of the patient.

BRIEF DESCRIPTION OF THE DRAWINGS

The invention may be understood by reference to the following description taken in conjunction with the accompanying drawings, in which like reference numerals identify like elements, and in which.

Figure 1A:
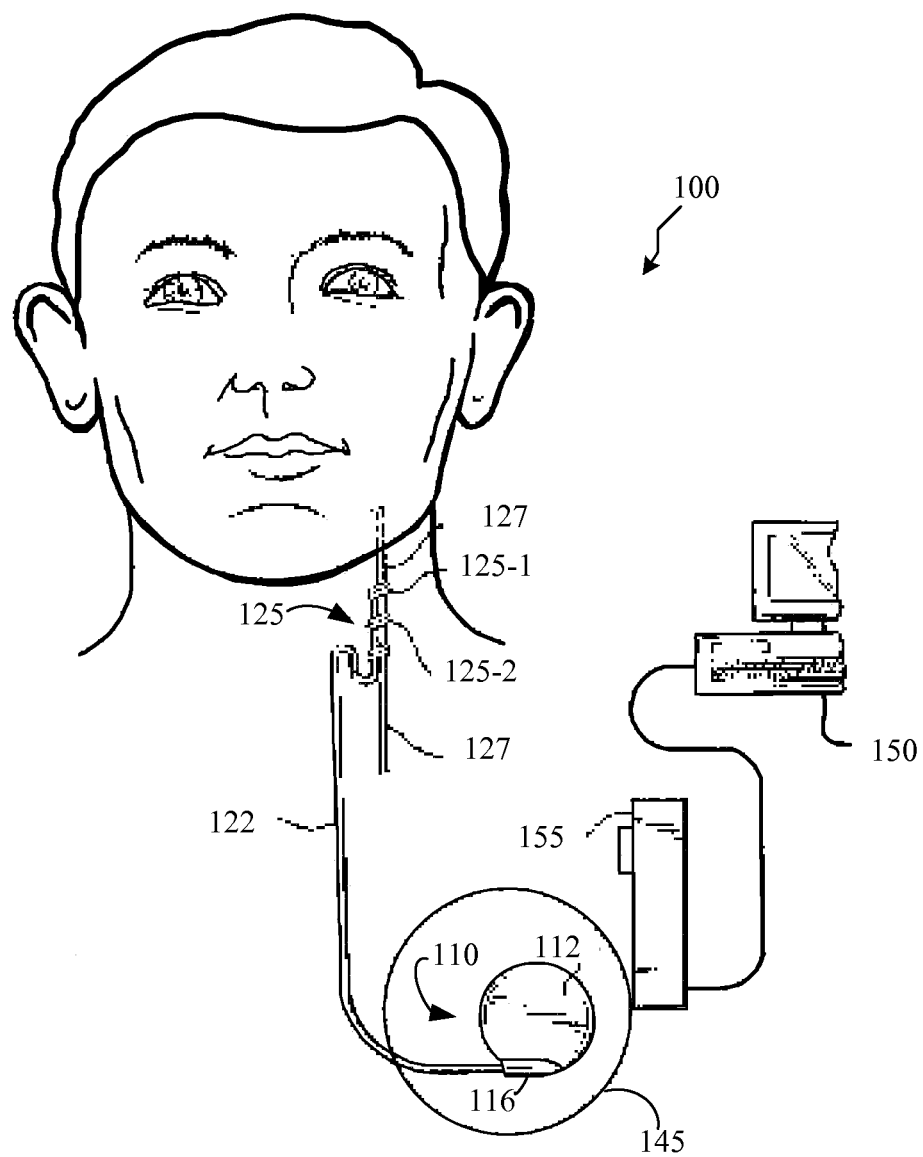
FIGS. 1A-1C provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

"Cardiac cycle" refers to one complete PQRSTU interval of the patient's heart functioning, ending with the P wave of the next succeeding cardiac cycle. "Interbeat interval" refers to the time period between a predetermined point in a first cardiac cycle of the patient and the same predetermined point in the immediately succeeding cardiac cycle of the patient, for example an R-R interval, a P-P interval, or a T-T interval. Interbeat intervals may comprise a single interval or a moving average (either simple or weighted) of several consecutive intervals. "Cardiac period" is a length of time between a first point in the cardiac cycle of the patient and a second, later point. Exemplary points include a P-wave, a Q-wave, an R-wave, an S-wave, a T-wave, and a U-wave of the cardiac cycle, which can be readily identified by electrocardiography (EKG) or other techniques of monitoring the electrical activity of the heart.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma and traumatic brain injury, coma, obesity, eating disorders, sleep disorders, cardiac disorders (such as congestive heart failure and atrial fibrillation), hypertension, endocrine disorders (such as diabetes and hypoglycemia), and pain syndromes (including migraine headache and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present invention provides a method of treating a medical condition. The medical condition can be selected from the group consisting of epilepsy, neuropsychiatric disorders (including but not limited to depression), eating disorders/obesity, traumatic brain injury/coma, addiction disorders, dementia, sleep disorders, pain, migraine, fibromyalgia, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including infertility). In a particular embodiment, the medical condition is epilepsy.

The implantable medical device (IMD) system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define the therapeutic electrical signals delivered by the IMD, medication parameters and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, an interburst period, a number of pulses per burst, an interpulse interval, a burst duration, an on-time, and an off-time.

In one embodiment of the present invention, an electrical signal may be provided in a duration that is determined as a function of a physiological cycle, e.g., a cardiac cycle. In one embodiment, the duration may be less than the physiological cycle, e.g., less than a cardiac cycle of the patient. In this manner, data relating to a parameter associated with the physiological cycle may be collected at times when the electrical signal is not provided. For example, by providing electrical signals to a vagus nerve 10 msec after detection of an R-wave in a patient's cardiac cycle, for a duration that is less than the prior cardiac cycle, it may be possible to sense the next R-wave without interference that may be associated with a signal applied for a duration longer than the patient's cardiac cycle. While techniques are available that would permit overlapping stimulation and sensing (such as blanking intervals in the signal, or use of separate sensing and stimulation electrodes), use of certain embodiments of the present invention renders such techniques unnecessary, and permits a simpler design. Even where stimulation durations longer than the cardiac cycle are used, the present invention may still allow the timing of later heartbeats to be predicted with sufficient accuracy (based on, for example, a moving average heartbeat) to avoid the use of separate sensing and stimulation electrodes.

Figure 1B:
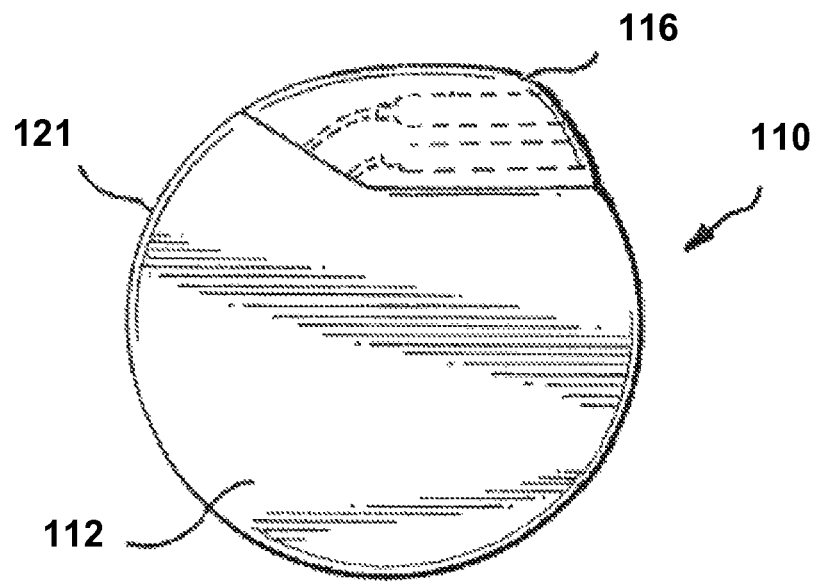
Figure 1C:
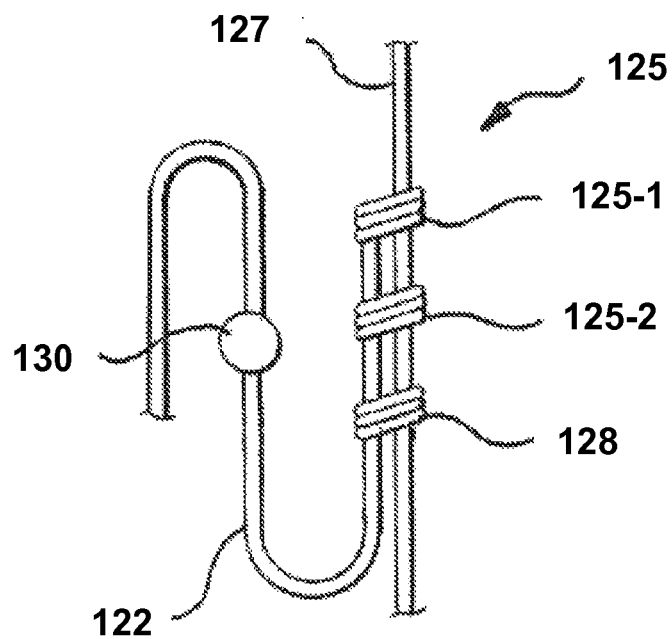

Although not so limited, a system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes with the return electrode comprising a portion of the generator 110.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used as a target for the electrical signal in particular alternative embodiments. In one embodiment, the electrode assembly 125 comprises a bipolar stimulating electrode pair 125(1), 125(2), 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed to trigger active stimulation. For example, motion sensors or electrodes may be used to sense respiration, and pressure sensors or neural activity may be used to sense blood pressure. Both passive and active stimulation may be combined or delivered by a single IMD according to the present invention. Either or both modes may be appropriate to treat a specific patient under observation.

In alternative embodiments, a sensor assembly, comprising a sensor lead assembly and a sensor, may be employed to detect a body parameter of the patient.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The therapeutic electrical stimulation signal described herein may be used to treat a medical condition separately or in combination with another type of treatment. For example, electrical signals according to the present invention may be applied in combination with a chemical agent, such as various drugs, to treat various medical conditions. Further, the electrical stimulation may be performed in combination with treatment(s) relating to a biological or chemical agent. The electrical stimulation treatment may also be performed in combination with other types of treatment, such as magnetic stimulation treatment.

Figure 2:
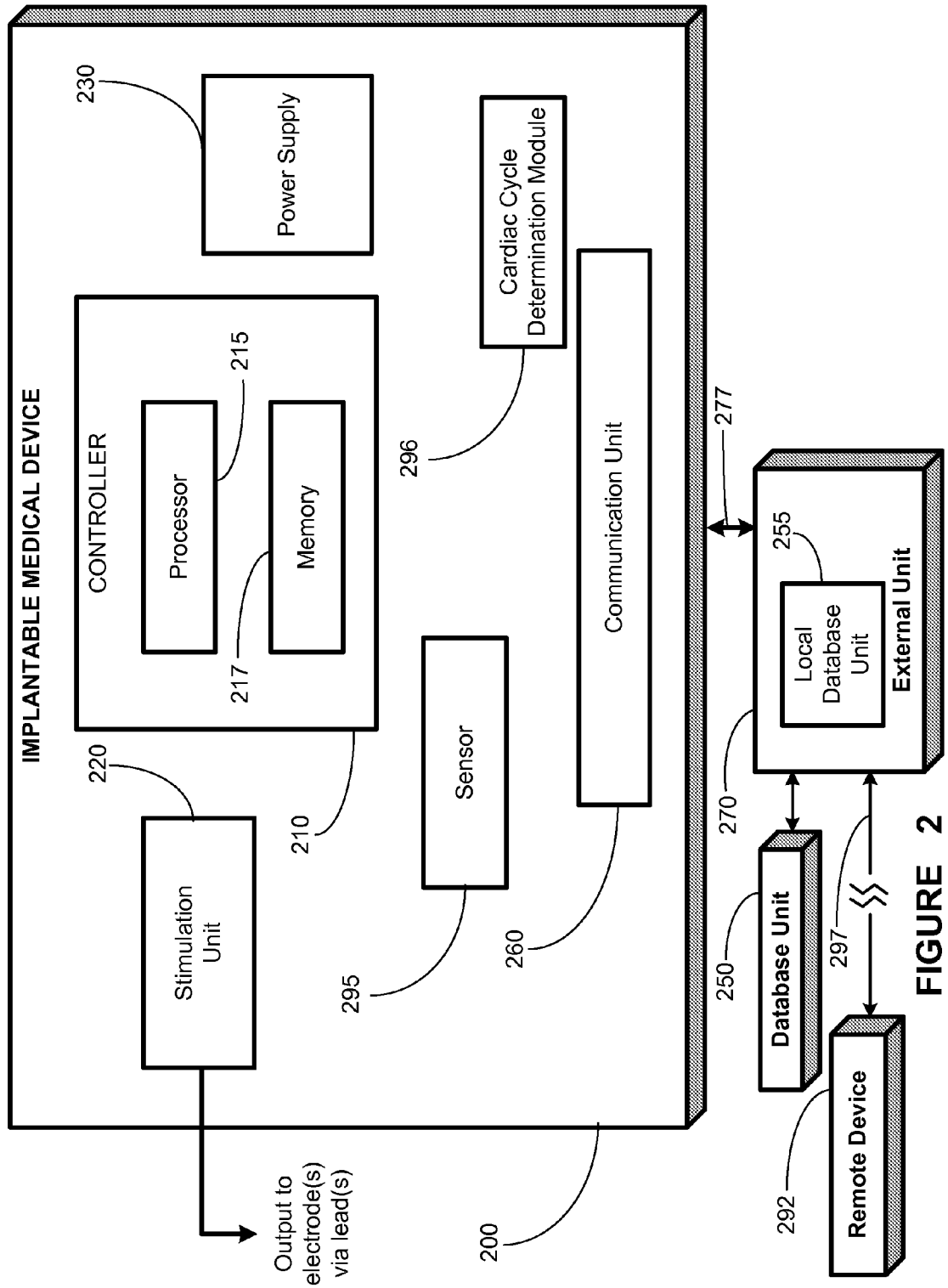
FIG. 2 illustrates a block diagram depiction of the implantable medical device of FIG. 1, in accordance with one illustrative embodiment of the present invention.

Turning now to FIG. 2, a block diagram depiction of the IMD 200 is provided, in accordance with one illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue.

The stimulation unit 220 is capable of delivering an electrical signal over the leads comprising the lead assembly 122. It will be appreciated by persons of skill in the art that some embodiments of the invention may comprise leadless stimulators such as injectable microstimulators.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 that may comprise an ED (FIG. 1). The communication unit 260 may include hardware, software, firmware, or any combination thereof.

In one embodiment, the IMD 200 may also comprise a sensor 295 that is capable of detecting various patient parameters. For example, the sensor 295 may comprise hardware, software, or firmware that is capable of obtaining and/or analyzing data relating to one or more body parameters of the patient. Based upon the data obtained by the detection unit 295, the IMD 200 may deliver or may refrain from delivering the electrical signal to a portion of the cranial nerve to treat epilepsy, depression or other medical conditions. In one embodiment, the sensor 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient. The term "patient parameters" may refer to, but is not limited to, various body parameters, which may in some embodiments involve sensors coupled to the IMD 200.

In another embodiment, the sensor 295 may be capable of sensing at least one parameter of a cardiac cycle of the patient. In a further embodiment, the at least one cardiac cycle parameter is selected from the group consisting of a P-wave, a Q-wave, an R-wave, an S-wave, a T-wave, and a U-wave, or intervals associated with the foregoing such as an R-R interval or another interbeat interval such as a T-T interval, a P-wave interval, a PR segment interval, a PQ segment interval, a QRS interval, an ST segment interval. However, in another embodiment, a separate sensor 295 is not included, and sensing at least one parameter of a cardiac cycle of the patient may be performed via one or more of the electrodes 125(1), 125(2) and/or the shell 112 of the IMD 200.

In another embodiment, the sensor 295 may comprise hardware, software, or firmware that is capable of obtaining and/or analyzing data relating to the patient's cardiac cycle. Based upon the data obtained by the detection unit 295, the IMD 200 may deliver the electrical signal to a portion of the cranial nerve to treat epilepsy, depression or other medical conditions.

In one particular embodiment, sensing is performed using the at least one electrode. In a further embodiment, the IMD 200 comprises an electrical signal generator; and a first electrode and a second electrode operatively coupled to the electrical signal generator and a cranial nerve of the patient; wherein: the electrical signal generator is capable of generating and delivering at least one electrical signal through at least one of the first electrode and the second electrode to the cranial nerve, when not delivering the electrical signal, at least one of the first electrode and the second electrode is capable of detecting the patient's heartbeat. Any point in the patient's cardiac cycle can be observed in order to detect the patient's heartbeat. In one embodiment, the patient's heartbeat is detected by detecting an R-wave.

In some embodiments, bipolar or unipolar stimulation can be interleaved with heartbeat detection. In one embodiment, during a first time period an electrical signal generated by the electrical signal generator is applied to the cranial nerve using both the first electrode and the second electrode. During a second time period following the first time period, the first and second electrodes are capable of detecting the patient's heartbeat, and the electrical signal generator does not apply the electrical signal to the cranial nerve. As an illustrative example, the first time period may begin from about 10 msec to about 3000 msec after a first heartbeat of the patient. The second time period follows the first time period and extends from the end of the first time period until detection of another heartbeat and application of the electrical to the cranial nerve following the detection. The first time period may be preceded by a delay time period following detection of a heartbeat (for example by detection of an R-wave) and before application of the electrical signal to the cranial nerve.

In one embodiment, the first time period defining the duration of the electrical signal being applied to the nerve may comprise a predetermined fraction of the cardiac cycle time of the patient. For example, the electrical signal generator may be programmed to apply the electrical signal to the nerve for a time equal to 10% of the moving average of the most recent n heartbeats (where n is an integer from 2 to 100, inclusive, such as an integer from 2 to 10, inclusive) as measured by the R-R interval, or 50% of the most recent single R-R interval. It will be appreciated that the duration could vary from as little as 0.1% of the cardiac cycle time, to times exceeding 100% of the cardiac cycle time, for example 250% of the cardiac cycle time. In a preferred embodiment, the cycle time would range from 1% to 50% of the cardiac cycle time, to permit adequate time for the IMD to cease applying the electrical signal and to detect the next heartbeat without electrical interference from the electrical signal itself. By defining the first time period as a percentage of the cardiac cycle time, the IMD system can provide a system with a well-defined duty cycle that automatically adjusts itself to changes in the patient's heart rate, without compromising the ability of the system to detect a heartbeat and/or determine a heart rate by interference from the electrical signal. In embodiments where separate sensing and stimulation electrodes are provided, first time periods greater than 100% of the cardiac signal may be employed without compromising the ability to detect a heartbeat and/or determine a heart rate.

Where a delay interval is used following detection of a heartbeat prior to the application of the signal during the first time period, the delay period may comprise either a fixed time period that may range from 1 µsec to 3000 msec, preferably from 5 msec to about 250 msec, or a programmable percentage of a moving average or single heartbeat interval. For example, the device may be programmed to provide a delay period equal to 5% of the moving average of the most recently detected R-R intervals.

The IMD 200 of this embodiment can further comprise a cardiac cycle determination module 296 capable of calculating the patient's heart rate. In one embodiment, the heart rate is calculated from the R-R interval of successive cardiac cycles. In a further embodiment, the electrical signal generator is capable of adjusting at least one parameter defining the electrical signal in response to the patient's heart rate. These adjustments may include adjusting at least one parameter associated with the electrical signal, e.g., a current amplitude, a pulse width, an interburst period, a number of pulses per burst, an interpulse interval, a burst duration, an on-time, and an off-time.

Figure 3A:
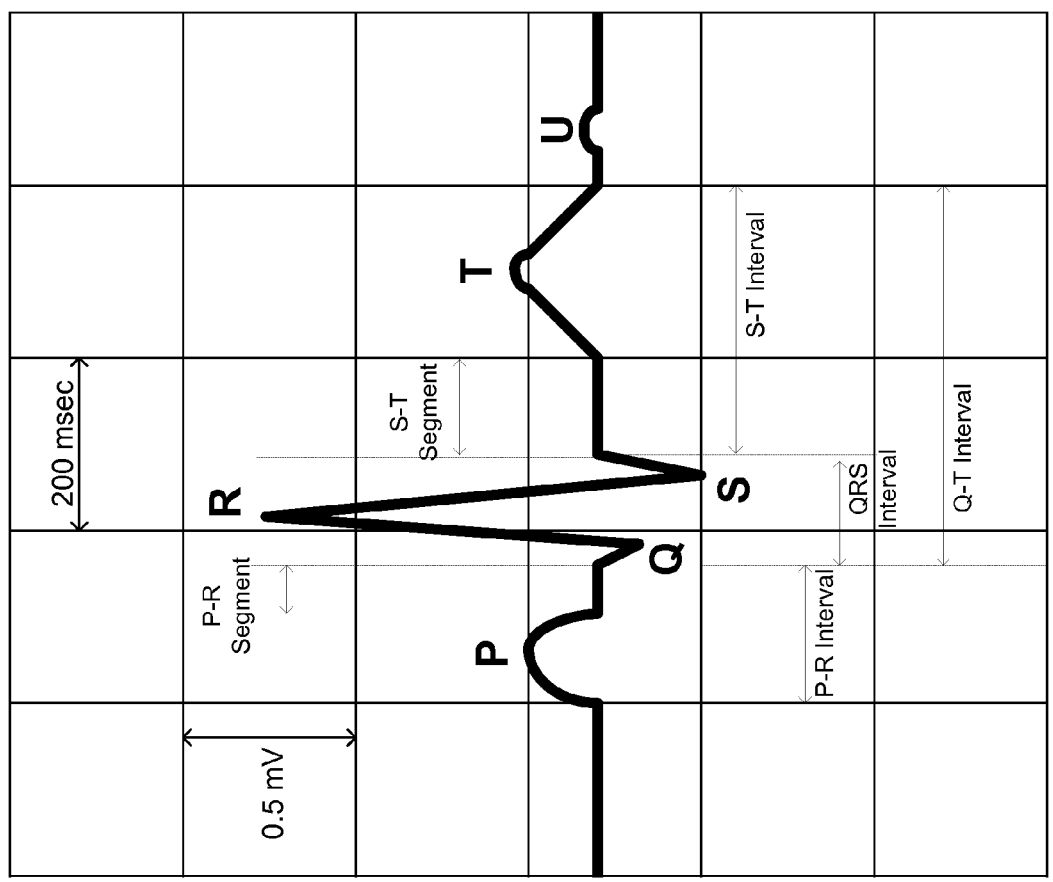
FIG. 3A illustrates an exemplary waveform sequence of a cardiac cycle of a human being as measured by an electrocardiogram (EKG)
Figure 3B:
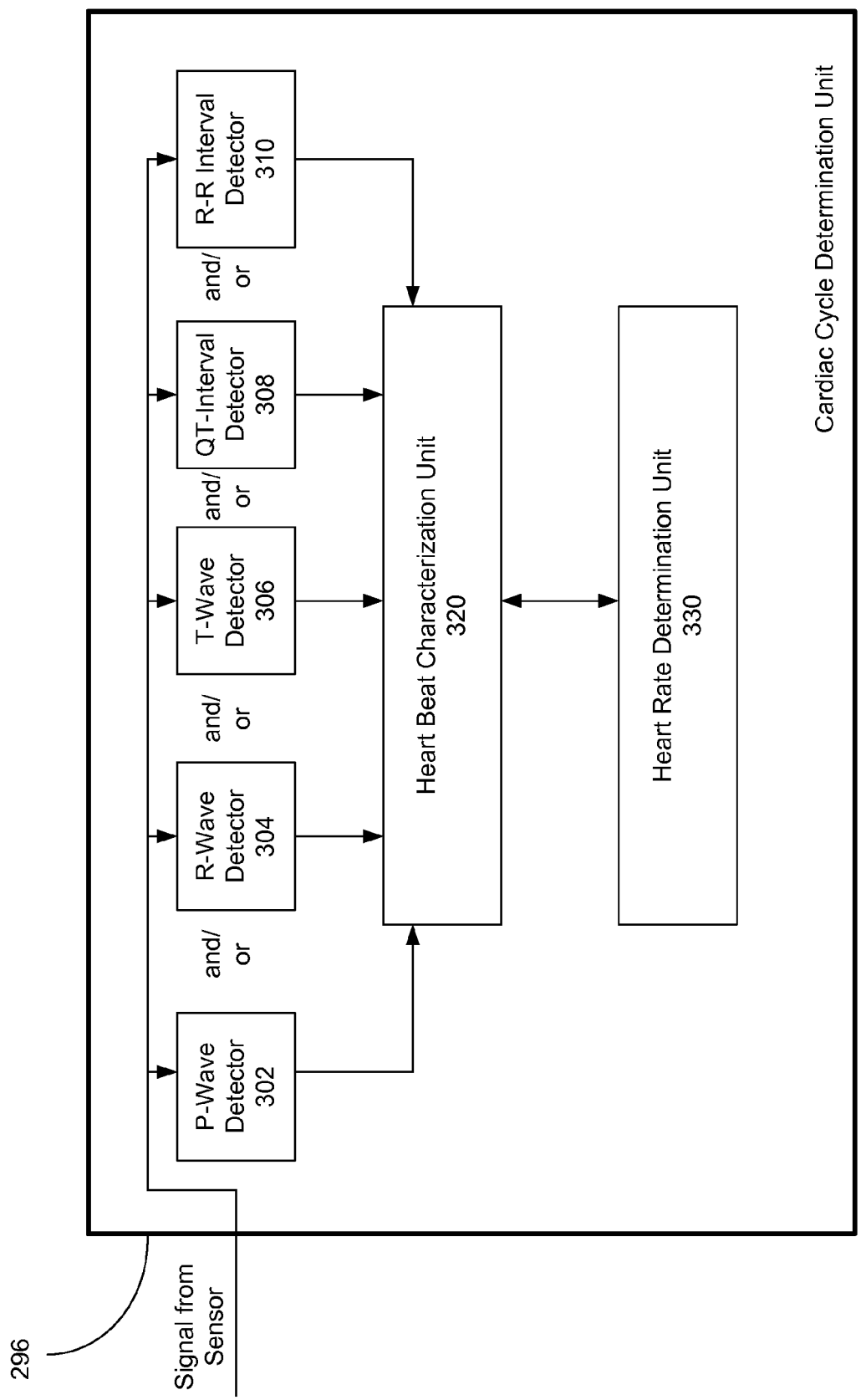
FIG. 3B illustrates a block diagram depiction of a cardiac cycle determination module of the implantable medical device of FIG. 2.

An illustrative embodiment of the cardiac cycle determination module 296 is shown in FIG. 3B. A signal from the sensor is delivered to one or more of a P-wave detector 302, an R-wave detector 304, a T-wave detector 306, a QT interval detector 308, or an R-R interval detector 310. The various detectors 302-310 communicate with the heart beat characterization unit 320, which takes data from the detectors 302-310 and characterizes whether a heart beat has taken place. The heart rate determination unit 330 can then track characterizations of heart beats and their times to determine a heart rate, either instantaneously (between two consecutive heart beats) or as an average, for example, a moving average of the last n heart beats, where n is an integer from 2 to 100, inclusive. In one further embodiment, n is an integer from 2 to 10, inclusive.

In a further embodiment, the cardiac period determination module 296 calculates an interbeat interval (either a single R-R interval or a moving average) and the electrical signal is applied to the target cranial nerve for a predetermined multiple (e.g., 0.1% to 3000%) of the calculated interbeat interval, optionally following a delay period that may be a fixed time period or a time period likewise defined as a predetermined multiple (e.g., 1-20%) of the calculated interbeat interval. Instead of defining a delay period and a first time period as a multiple of the calculated interbeat interval, the beginning and ending timepoints of the first time period can equivalently be selected as occurred at selected points within the calculated interbeat interval following the detected heartbeat. For example, the stimulation can be programmed to begin at a timepoint that is 5% of the calculated interbeat interval following the detection of the heartbeat, and to end at a timepoint that is 15% of the calculated interbeat interval following detection of the heartbeat. In another embodiment, the stimulation may be synchronized with the detection of a P wave, a T wave, or other points within the cardiac cycle, such as beginning at the T wave detection and extending for a duration that is, for example, 20% of the calculated interbeat interval.

In one embodiment, the first time period has a duration of from about 5% to about 50% of the calculated interbeat interval. The first time period is followed by a second time period during which the IMD senses the next heartbeat, recalculates the interbeat interval, and again applies the electrical signal to the nerve for a predetermined percentage of the recalculated interbeat interval.

Although the above description is in the context of bipolar stimulation, the person of ordinary skill in the art, having the benefit of the present disclosure, will understand the IMD 200 may also or alternatively be capable of detecting a heartbeat during unipolar stimulation.

The characteristic of the cardiac cycle, after which initiation of delivery of the electrical signal is initiated, may be varied during operation of the IMD 200.

In one embodiment, the IMD 200 may comprise a cardiac cycle determination module 296. The cardiac cycle determination module 296 may be capable of analyzing the at least one sensed characteristic of the patient's cardiac cycle and determining at least one cardiac cycle parameter. In a further embodiment, the at least one cardiac cycle parameter is selected from the group consisting of an R-R interval, a P wave interval, a PR segment interval, a PQ segment interval, a QRS interval, an ST segment interval, and a QT interval, or an interbeat interval. The determined cardiac cycle parameter (s) may be used for synchronization of the stimulation and/or for determination of the duration of stimulation The external unit 270 may be a device that is capable of programming the IMD 200 with parameters defining the electrical signal. In one embodiment, the external unit 270 is a computer system capable of executing a data-acquisition program. The external unit 270 may be controlled by a healthcare provider, such as a physician, at a base station in, for example, a doctor's office, or via telemetry from a doctor's office to a patient's home. In alternative embodiments, the external unit 270 may be controlled by a patient in a system. In patient-controlled systems, the external unit 270 may provide less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may upload various parameters and program software into the IMD 200 for programming the operation of the IMD, and may also receive and download various status conditions and other data from the IMD 200. Communications between the external unit 270 and the communication unit 260 in the IMD 200 may occur via a wireless or other type of communication, represented generally by line 277 in FIG. 2. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions using the external unit 270, which may include obtaining and/or analyzing data from the IMD 200 and/or data from the database unit 250 and/or the local database unit 255. The database unit 250 and/or the local database unit 255 may store various patient data.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110. Two taps spaced apart by a slightly longer duration of time may be programmed into the IMD 100 to indicate a desire to deactivate the electrical signal generator 110, for example. The patient may be given limited control over operation of the device to an extent determined by the program dictated or entered by the attending physician. The patient may also activate the IMD 100 using other suitable techniques or apparatus.

In some embodiments, a cranial nerve stimulation system may include a sensing lead coupled at its proximal end to a header along with a stimulation lead and electrode assemblies. A sensor may be coupled to the distal end of the sensing lead. The sensor may include a cardiac cycle sensor. The sensor may also include a nerve sensor for sensing activity on a nerve, such as a cranial nerve, such as the vagus nerve 127.

In one embodiment, the sensor may sense a body parameter that corresponds to a symptom of a medical condition. If the sensor is to be used to detect a symptom of the medical condition, a signal analysis circuit may be incorporated into the IMD 100 for processing and analyzing signals from the sensor. Upon detection of the symptom of the medical condition, the processed digital signal may be supplied to a microprocessor in the IMD 100 to trigger application of the electrical signal to the cranial nerve, such as vagus nerve 127. In another embodiment, the detection of a symptom of interest may trigger a stimulation program comprising different stimulation parameters from a passive stimulation program. This may entail providing a higher current stimulation signal or providing a higher ratio of on-time to off-time.

FIG. 3A shows an exemplary instance of the cardiac cycle in a human being.

In one embodiment, the first point in the cardiac cycle is an R-wave and the second point in the cardiac cycle is the next R-wave, i.e., in this embodiment, the cardiac cycle is determined by an R-R interval and the interbeat interval is the R-R interval.

The interbeat interval can be determined from actual, particular cardiac data, or it can be calculated from actual, particular cardiac data. In one embodiment, the interbeat interval is a moving average R-R interval calculated over the last n R-R intervals, where n is an integer from 2 to about 100. The moving average can be a simple moving average, an exponential moving average, or another non-simple moving average, although a simple moving average is preferred. In a further embodiment, n is 3 in the calculation of the simple moving average.

The duration of applying can be less than, the same as, or greater than an interbeat interval of the patient. In one embodiment, the duration of applying is less than an R-R interval of the patient's cardiac cycle. In a further embodiment, the R-R interval is selected from the group consisting of an R-R interval immediately preceding the most recently detected R-wave, and a moving average R-R interval calculated over the last n R-R intervals, where n is an integer from 2 to about 100. In a further embodiment, n is 3.

The duration of applying may be determined from selected durations in a cardiac cycle of the patient, for example an ST segment duration, a PQ interval, or may comprise a percentage of an actual or calculated interbeat interval. In embodiments wherein the duration of applying is a percentage of an interbeat interval, the duty cycle of the IMD 200 may be a known ratio of on-time to off-time, which may be desirable in predicting useful battery life or device life. In one embodiment, the duration of applying is a percentage of the R-R interval, for example, from 0.1% of the R-R interval to 3000% or more of the R-R interval, or in a further embodiment, from 10% of the R-R interval to 50% of the R-R interval. The person of ordinary skill in the art will understand other cardiac periods could be the basis on which the duration of applying as a percentage thereof is calculated.

The electrical signal may be applied to the cranial nerve immediately after a predetermined point in the cardiac cycle or after a delay period following the predetermined point in the cardiac cycle. In this context, "immediately after" refers to less than ten microseconds after the IMD 200 detects the predetermined point in the cardiac cycle, e.g., an event selected from the group consisting of a P-wave, a Q-wave, an R-wave, an S-wave, a T-wave, and a U-wave, and processes the detection to yield a decision to apply the electrical signal.

When the electrical signal is applied after a delay period following the predetermined point in the cardiac cycle, the delay period can be from 0.1 msec to about 1000 msec.

In one illustrative embodiment, the electrical signal may be applied to the cranial nerve after a selected number of cardiac cycles. The selected number or cardiac cycles may be one (i.e., the electrical signal is applied during every cardiac cycle) or any integer greater than one. The IMD 200 may reselect the selected number of cardiac cycles during operation, for example, in response to data received regarding the patient's medical condition.

In another illustrative embodiment, the electrical signal may be applied to the cranial nerve after a selected length of clock time has passed. In one embodiment, the selected length of clock time is from 10 seconds to 30 minutes.

Embodiments of the present invention may also be combined with conventional neurostimulation in which the duration of the signal is independent of the cardiac cycle of the patient. For example, embodiments of the invention may be used to provide stimulation for short periods determined as a function of the cardiac cycle of the patient to allow the determination of moving averages of the patient's interbeat interval, and to provide stimulation bursts for much longer periods of time when the patient's cardiac cycle experiences rapid changes. For example, in epilepsy, many patients experience tachycardia (elevated heart rate) before or during a seizure. On the other hand, some epilepsy patients experience bradycardia (lowering of heart rate) before or during a seizure. In one embodiment, upon detecting tachycardia, the IMD 200 may apply an electrical stimulation for a predetermined time period that is independent of the cardiac cycle of the patient, for example 30 seconds, 1 minute, or shorter or longer fixed periods. In another embodiment, upon detecting bradycardia, the IMD 200 may likewise apply an electrical signal for a duration that is independent of the cardiac cycle of the patient. Neurostimulation independent of the cardiac cycle may be chosen to minimize the change in heart rate, the duration of the heart rate change, or both, in cases of tachycardia or bradycardia, but it need not be so chosen.

Figure 4:
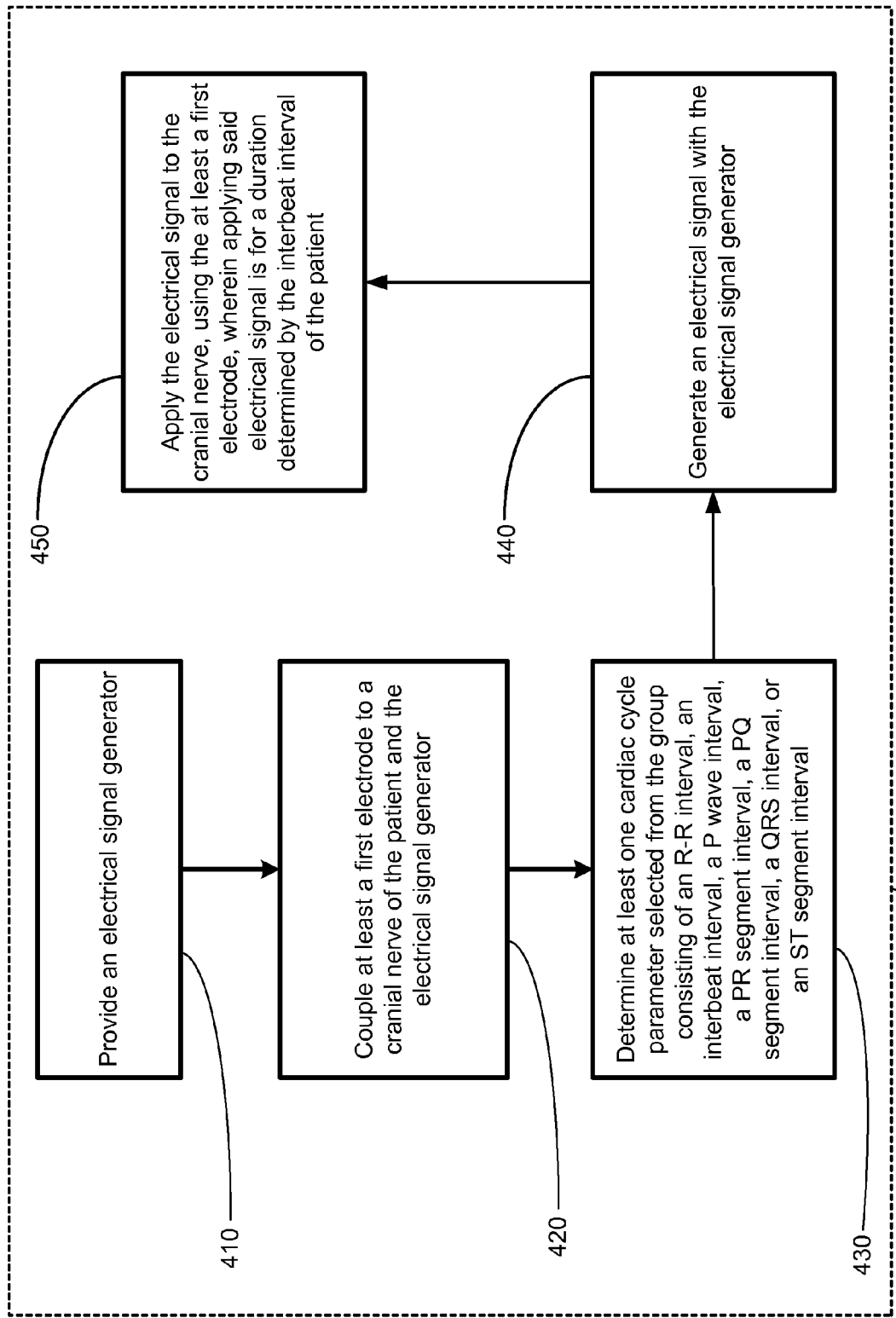
FIG. 4 illustrates a flowchart depiction of a method in accordance with an illustrative embodiment of the present invention.

Turning now to FIG. 4, a flowchart depiction of a method 400 for treating a medical condition in accordance with one illustrative embodiment of the present invention is shown. An electrical signal generator is provided (block 410) and at least a first electrode is coupled to a cranial nerve of the patient and the electrical signal generator (block 420). The one or more electrodes may be operatively coupled to at least one of a main trunk of the right or left vagus nerve, or any branch thereof. The IMD may determine at least one cardiac cycle parameter, which may be selected from the group consisting of an R-R interval or another interbeat interval, a P wave interval, a PR segment interval, a PQ segment interval, a QRS interval, or an ST segment interval (block 430). The IMD 100 may then generate an electrical signal (block 440).

The IMD 100 may then apply the electrical signal to the cranial nerve (block 450). The application of the electrical signal may be delivered to the main trunk of the right or left vagus nerve, or any branch thereof The duration of applying is determined by the at least one cardiac cycle parameter of the patient.

Using embodiments of the present invention, a therapeutic regimen comprising neurostimulation may be enhanced and optimized. Using certain embodiments, data either directly or indirectly associated with an acute incident of a medical condition may be collected, in order to inform the patient and/or his physician about the severity, progression, or remission of the medical condition.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method of providing an electrical signal to a cranial nerve of a patient for treating a medical condition, comprising:
   a) determining a cardiac cycle duration of at least a portion of a cardiac cycle;

b) determining a stimulation duration which is based on a predetermined fraction of the determined cardiac cycle duration, wherein the predetermined fraction is less than one;

c) generating an electrical signal based on the stimulation duration;

d) applying the electrical signal to the cranial nerve for the stimulation duration, wherein the electrical signal is operative to deliver an electrical signal stimulation to a patient's brain via the cranial nerve; and e) repeating a-d to automatically adjust the stimulation duration based on changes in the at least a portion of the cardiac cycle.

2. The method of claim 1 wherein at least the portion of the cardiac cycle includes at least one of an R-R interval, a P-P interval, a T-T interval, a P wave interval, a PR segment interval, a PQ segment interval, a QRS interval, an ST segment interval, and an interbeat interval of the patient.

3. The method of claim 2, wherein the stimulation duration is less than the interbeat interval.

4. The method of claim 3, wherein the stimulation duration is determined by reference to the interbeat interval based on at least one of the R-R interval immediately preceding a most recently detected R-wave, and a moving average R-R interval calculated over a last n R-R intervals, where n is an integer from 2 to about 10.

5. The method of claim 2, wherein the stimulation duration is greater than the interbeat interval.

6. The method of claim 1, wherein the stimulation duration is from 10% of an interbeat interval to 50% of the interbeat interval.

7. The method of claim 1, wherein applying the electrical signal to the cranial nerve comprises beginning to apply the electrical signal at a particular point in the cardiac cycle of the patient.

8. The method of claim 7, wherein the particular point in the cardiac cycle is based on at least one of a detected P-wave, a detected Q-wave, a detected R-wave, a detected S-wave, a detected T-wave, and a detected U-wave.

9. The method of claim 7, wherein the particular point in the cardiac cycle follows a point in the cardiac cycle based on a period which includes a delay period and at least one of a detected P-wave, a detected Q-wave, a detected R-wave, a detected S-wave, a detected T-wave, and a detected U-wave.

10. The method of claim 9, wherein the delay period is from 0.1 msec to about 1000 msec.

11. The method of claim 1, wherein applying the electrical signal to the cranial nerve comprises beginning to apply the electrical signal after a selected number of occurrences of at least one of a detected P-wave, a detected Q-wave, a detected R-wave, a detected S-wave, a detected T-wave, and a detected U-wave.

12. The method of claim 11, wherein applying the electrical signal to the cranial nerve comprises beginning to apply the electrical signal after a predetermined number of R-waves ranging from two R-waves to 1000 R-waves.

13. The method of claim 1, further comprising:

sensing at least one parameter of the cardiac cycle of the patient based on at least one of a P-wave, a Q-wave, an R-wave, an S-wave, a T-wave, and a U-wave, and determining the stimulation duration at least partially based on at least one sensed parameter of the cardiac cycle.

14. An implantable medical device (IMD), comprising:

an electrical signal generator; and a cardiac cycle determination module configured to determine a cardiac cycle duration of at least a portion of a cardiac cycle of a patient; wherein:

the electrical signal generator is configured to provide an electrical signal to a target tissue via a first electrode for a stimulation duration, wherein the stimulation duration is based on a predetermined fraction of a determined cardiac cycle duration, wherein the predetermined fraction is less than one, the stimulation duration being automatically adjusted in response to changes in the at least a portion of the cardiac cycle of the patient; and wherein the electrical signal is operative to deliver an electrical signal stimulation to a patient's brain.

15. The implantable medical device of claim 14, wherein the electrical signal is initiated at a time determined by at least one cardiac cycle parameter.

16. The implantable medical device of claim 14, wherein the stimulation duration is determined by reference to an interbeat interval based on at least one of an R-R interval immediately preceding a most recently detected R-wave, and a moving average R-R interval calculated over a last n R-R intervals, where n is an integer from 2 to about 10.

17. An implantable medical device, comprising:

an electrical signal generator; and a cardiac cycle determination module adapted to determine a cardiac cycle duration of a patient; and wherein the electrical signal generator is configured to generate and to deliver at least one electrical signal to a target tissue via a first electrode; and wherein a stimulation duration of a delivery of the at least one electrical signal is a predetermined fraction of a determined cardiac cycle duration, wherein the predetermined fraction is less than one, the stimulation duration being automatically adjusted in response to changes in a heart parameter of the patient.

18. The implantable medical device of claim 17, wherein the cardiac cycle duration is an interbeat interval which is based on at least one of a last detected interbeat interval and a moving average interbeat interval calculated over a last n interbeat intervals, where n is an integer from 2 to about 10.

19. The implantable medical device of claim 17, wherein the predetermined fraction may be automatically adjusted based on a determined condition of the patient.

* * * * *